(12) United States Patent
Miller et al.

(10) Patent No.: US 12,318,124 B2
(45) Date of Patent: Jun. 3, 2025

(54) CONTINUOUS FIBER BONE SCREW AND METHOD OF MANUFACTURE

(71) Applicant: Warsaw Orthopedic, Inc., Warsaw, IN (US)

(72) Inventors: Keith E. Miller, Germantown, TN (US); Brian A. Butler, Millington, TN (US); William A. Rezach, Covington, TN (US); Jonathan M. Dewey, Memphis, TN (US); Jeffrey W. Beale, Bartlett, TN (US); Julien J. Prevost, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 553 days.

(21) Appl. No.: 17/536,787

(22) Filed: Nov. 29, 2021

(65) Prior Publication Data
US 2023/0165613 A1 Jun. 1, 2023

(51) Int. Cl.
*A61B 17/86* (2006.01)
*A61B 17/70* (2006.01)
(Continued)

(52) U.S. Cl.
CPC ........ *A61B 17/861* (2013.01); *A61B 17/7032* (2013.01); *B29D 1/005* (2013.01);
(Continued)

(58) Field of Classification Search
CPC ............ A61B 17/8625; A61B 17/8635; A61B 17/866; A61B 17/8685
See application file for complete search history.

(56) References Cited

U.S. PATENT DOCUMENTS 2,993,950 A * 7/1961 Forman ................. F16B 35/044
174/209
3,604,487 A 9/1971 Gilbert
(Continued)

FOREIGN PATENT DOCUMENTS

| CN | 113209389 A | 8/2021 |
|---|---|---|
| DE | 10319781 B3 | 8/2004 |

(Continued)

OTHER PUBLICATIONS

International Search Report and Written Opinion in Application No. PCT/IB2022/000798 dated Oct. 30, 2023.

*Primary Examiner* — Nicholas W Woodall
(74) *Attorney, Agent, or Firm* — FOX ROTHSCHILD LLP (57) ABSTRACT

The present disclosure provides for a bone screw formed of continuous fibers, for example. The bone screw may include a first portion having a cylindrical shape and extending in a longitudinal direction from a first end to a second end, for example. In various embodiments, the first portion may include a thermoplastic material and/or be substantially formed of a thermoplastic material. In various embodiments, the bone screw may include a second portion coupled to the first portion and surrounding the first portion, at least partly, for example. In various embodiments, the second portion may include a plurality of layers, each layer comprising a continuous fiber material, for example. In various embodiments, the continuous fibers may be oriented longitudinally, diagonally, helically, radially, etc. In various embodiments, the second portion may define an exposed thread pattern and a leading tip.

16 Claims, 9 Drawing Sheets

(51) Int. Cl.
*B29D 1/00* (2006.01)
*B33Y 80/00* (2015.01)
*A61B 17/00* (2006.01)
*A61B 90/00* (2016.01)

(52) U.S. Cl.
CPC ..... *B33Y 80/00* (2014.12); *A61B 2017/00955* (2013.01); *A61B 2090/3983* (2016.02)

(56) References Cited

U.S. PATENT DOCUMENTS

| | | | |
|---|---|---|---|
| 3,844,291 | A | 10/1974 | Moen |
| 4,044,170 | A | 8/1977 | Scharbach et al. |
| 4,411,259 | A | 10/1983 | Drummond |
| 5,020,519 | A | 6/1991 | Hayes et al. |
| 5,113,685 | A | 5/1992 | Asher et al. |
| 5,177,958 | A | 1/1993 | Clemens et al. |
| 5,314,431 | A | 5/1994 | Graziano |
| 5,330,472 | A | 7/1994 | Metz-Stavenhagen |
| 5,360,448 | A | 11/1994 | Thramann |
| 5,364,397 | A | 11/1994 | Hayes et al. |
| 5,389,099 | A | 2/1995 | Hartmeister et al. |
| 5,395,371 | A | 3/1995 | Miller et al. |
| 5,449,361 | A | 9/1995 | Preissman |
| 5,458,608 | A | 10/1995 | Wortrich |
| 5,466,243 | A | 11/1995 | Schmieding et al. |
| 5,616,143 | A | 4/1997 | Schlapfer et al. |
| 5,643,263 | A | 7/1997 | Simonson |
| 5,720,751 | A | 2/1998 | Jackson |
| 5,782,830 | A | 7/1998 | Farris |
| 5,810,821 | A | 9/1998 | Vandewalle |
| 5,824,247 | A | 10/1998 | Tunc |
| 5,899,901 | A | 5/1999 | Middleton |
| 5,910,141 | A | 6/1999 | Morrison et al. |
| 5,944,720 | A | 8/1999 | Lipton |
| 5,947,967 | A | 9/1999 | Barker |
| 6,036,692 | A | 3/2000 | Burel et al. |
| 6,042,582 | A | 3/2000 | Ray |
| 6,063,088 | A | 5/2000 | Winslow |
| 6,152,927 | A | 11/2000 | Farris et al. |
| 6,280,445 | B1 | 8/2001 | Morrison et al. |
| 6,440,133 | B1 | 8/2002 | Beale et al. |
| 6,740,086 | B2 | 5/2004 | Richelsoph |
| 6,783,527 | B2 | 8/2004 | Drewry et al. |
| 6,916,321 | B2 | 7/2005 | TenHuisen et al. |
| 7,235,079 | B2 | 6/2007 | Jensen et al. |
| 7,575,572 | B2 * | 8/2009 | Sweeney ............ A61B 17/8685 604/264 |
| 7,850,717 | B2 * | 12/2010 | Dewey ............... A61B 17/8625 606/76 |
| 8,591,584 | B2 | 11/2013 | Reah et al. |
| 9,090,029 | B2 | 7/2015 | Prevost |
| 9,492,210 | B2 | 11/2016 | Rains et al. |
| 10,617,458 | B2 * | 4/2020 | Beyar ................... A61B 90/39 |
| 11,730,866 | B2 * | 8/2023 | Preiss-Bloom ......... A61L 31/08 606/331 |
| 2005/0059972 | A1 | 3/2005 | Biscup |
| 2005/0240265 | A1 | 10/2005 | Kuiper et al. |
| 2009/0093819 | A1 | 4/2009 | Joshi |
| 2010/0063550 | A1 * | 3/2010 | Felix ................... A61B 17/866 606/301 |
| 2011/0106162 | A1 | 5/2011 | Ballard et al. |
| 2013/0237813 | A1 | 9/2013 | Beyar et al. |
| 2015/0327893 | A1 | 11/2015 | Beyar et al. |
| 2016/0113695 | A1 | 4/2016 | Globerman et al. |
| 2019/0151000 | A1 * | 5/2019 | Kane .................. A61B 17/8615 |
| 2019/0167310 | A1 | 6/2019 | Felix et al. |
| 2020/0345895 | A1 | 11/2020 | Preiss-Bloom et al. |
| 2021/0244860 | A1 | 8/2021 | Williams et al. |

FOREIGN PATENT DOCUMENTS

| | | |
|---|---|---|
| GB | 2073024 A | 10/1981 |
| WO | 2022111826 A1 | 6/2022 |

* cited by examiner

CONTINUOUS FIBER BONE SCREW AND METHOD OF MANUFACTURE

CROSS-REFERENCE TO RELATED APPLICATIONS

This application incorporates by reference the entire disclosure of U.S. patent application Ser. No. 17/515,715, titled BONE SCREW HAVING AN OVERMOLD OF A SHANK, filed on Nov. 1, 2021 and U.S. Pat. No. 7,850,717, titled Bone anchors having two or more portions exhibiting different performance characteristics and method of forming the same, filed on Mar. 1, 2006.

FIELD

The present technology is generally related to bone screws for use in a medical context that may be formed of continuous fibers layered in a composite, laminated 2D or 3D structure. Example continuous fibers may include carbon fibers or glass fibers, for example. In some embodiments, a bone screw may be formed by a 3D printing technology and/or additive manufacturing process that orients a continuous fiber in various orientations to achieve the desired mechanical performance in the desired modes of expected loading. In some embodiments, a bone screw may be formed by utilizing a first portion as a substrate and then adding a second portion on top of the first portion. The second portion may be formed on top of the first portion by layering continuous fibers. In some embodiments, the continuous fibers may be surrounded by an extrudate serving as a carrier and the continuous fibers and extrudate may be extruded from an extruder onto the substrate.

BACKGROUND

A bone screw and/or pedicle screw may be implanted in a human patient for a variety of medical uses. At least one use involves the installation of a pedicle screw into a boney anatomy of a patient and the subsequent attachment of a receiver or connector to the pedicle screw for stabilization and/or fixation of the boney anatomy. Conventional bone screws and pedicle screws are formed of metallic materials, which are highly visible on an X-ray, and in some unwanted circumstances may block and/or otherwise hinder visibility of certain elements of patient anatomy.

SUMMARY

The present technology is generally related to bone screws for use in a medical context that may be formed of a first portion comprising a thermoplastic material and a second portion comprising continuous fibers that are layered on top of the first portion to achieve a desired mechanical strength in all modes of loading.

In one aspect, the present disclosure provides for a bone screw, including a first portion having a cylindrical shape and extending in a longitudinal direction from a first end to a second end, for example. In various embodiments, the first portion may include a thermoplastic material and/or be substantially formed of a thermoplastic material. In various embodiments, the bone screw may include a second portion coupled to the first portion and surrounding the first portion, at least partly, for example. In various embodiments, the second portion may include a plurality of layers, each layer comprising a continuous fiber material, for example. In various embodiments, the continuous fibers may be oriented longitudinally, diagonally, helically, radially, etc. In various embodiments, the second portion may define an exposed thread pattern and a leading tip.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-6 generally, various bone screws 100 are disclosed. The components of bone screw 100 can be fabricated from biologically acceptable materials suitable for medical applications, including metals, synthetic polymers, ceramics and bone material and/or their composites. For example, the components, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Figure 1A:
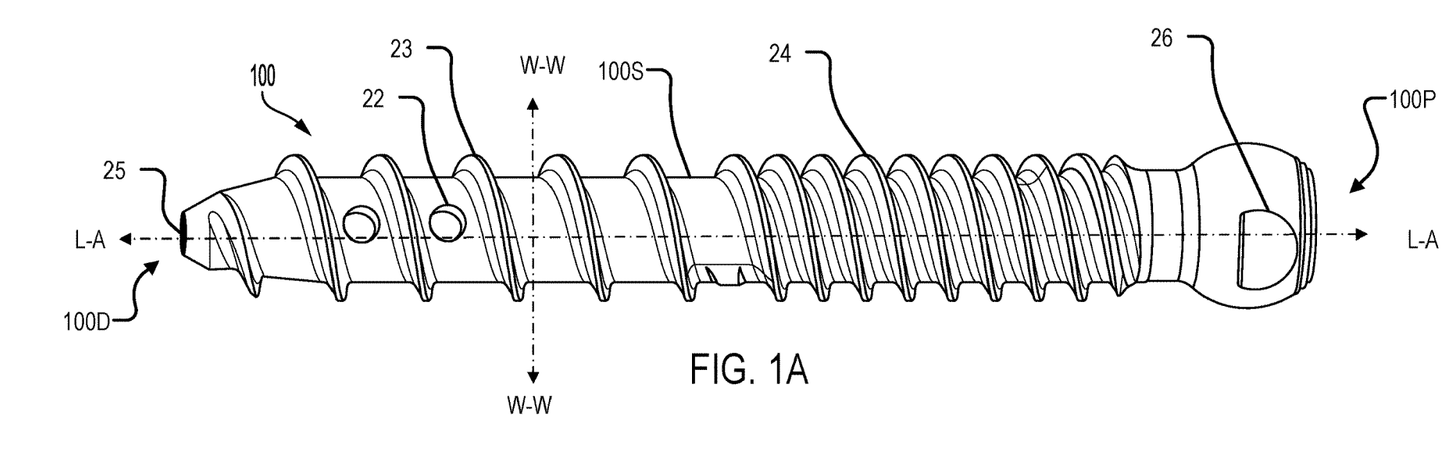
FIG. 1A is a side view of a bone screw.
Figure 1B:
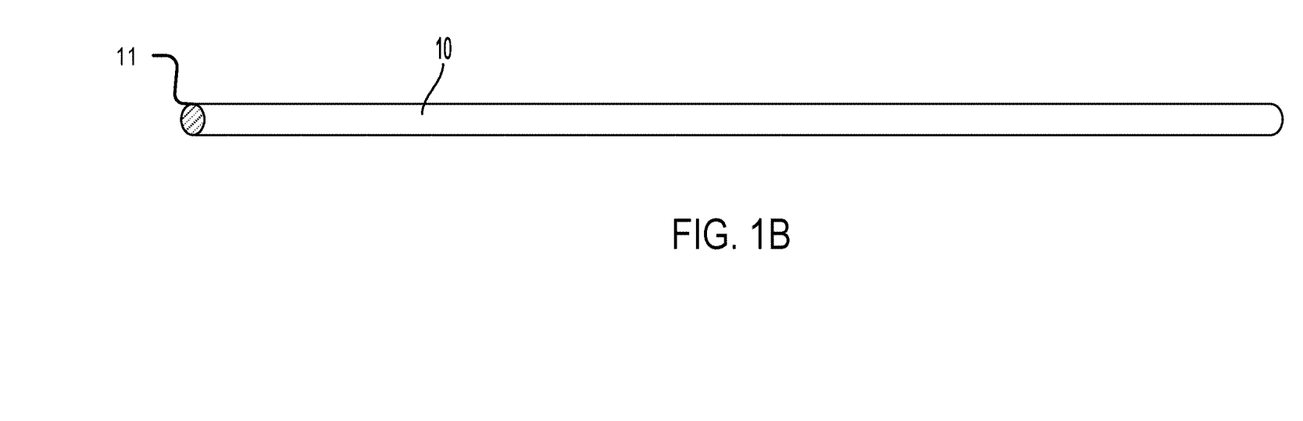
FIG. 1B is a side view of a substrate for forming the bone screw of FIG. 1.

FIG. 1A is a side view of a bone screw 100 and FIG. 1B is a side view of a substrate 10 for forming the bone screw 100 of FIG. 1, for example. In various embodiments substrate 10 may be formed of a plastic or thermoplastic material, e.g., PEEK, PEKK, Nylong, and/or Short Fiber PEEK, for example. Substrate 10 may serve as a base and/or first portion during a method of manufacture of bone screw 100. For example, substrate 10 may be a stock material and continuous fibers, e.g., Carbon Fiber and/or Glass Fibers, may be layered on top of substrate 10 to form bone screw 100. As used herein, the term "continuous fiber" shall have its ordinary technical meaning as understood by persons of ordinary skill in the art unless the context clearly indicates otherwise. In various embodiments, a continuous fiber and/or continuous fiber layer does not necessarily require that each fiber is continuous along the length thereof but that an average of the fibers extend in a continuous direction, e.g., individual fibers may be lapped. However, the term "continuous fiber" shall be understood to have a distinct meaning from "randomly oriented fibers" and/or "chopped fibers" as would be understood by a person of ordinary skill in the art. At least one understanding of the term "continuous fibers" may be a plurality of fibers that are generally extending in the same direction and/or geometric pattern, i.e., parallel and/or substantially parallel. By way of a non-limiting example, a continuous fiber may be geometrically characterized as having a very high length-to-diameter ratio. In some embodiments, continuous fiber diameters may generally range between about 0.00012 μin and 0.0074 μin (3-200 μm), depending upon the fiber. However, other diameters are contemplated and fall within the scope of the term "continuous fiber."

Substrate 10 may take any shape, e.g., an elongate shape such as a cylinder, conical tapering shape, frustoconical shape, rectangular shape, etc. In various embodiments, the fibers may be considered continuous and may be laminated as a 2D or 3D structure using 3D printing technology to achieve various desirable mechanical characteristics under loading, e.g., flexural strength, compressive strength, tensile strength, elasticity, hardness, etc. In the example embodiment, bone screw 100 may extend in a longitudinal direction from a proximal end 100P to a distal end 100D along longitudinal axis L-A, for example. Additionally, bone screw 100 may extend in a widthwise direction (may also be referred to as lateral direction) between sidewall surfaces 100S along widthwise axis W-W. The proximal end 100P may include a head 26 having any type of drive interface, for example hexalobular, torx, square, polygonal, and combinations thereof. The medial portion of bone screw 100 may include various features such as at least one thread pattern 23, 24, and fenestrations 22. The distal end 100D may include a tip 25. In some embodiments, tip 25 of bone screw 100 may be coextensive and/or defined by end 11 of substrate 10. For example, substrate 10 may include a metallic tip which may also define a metallic tip 25 of bone screw 100. Some advantages to a metallic tip may include durability during driving and serving as a fiducial marker for radiolucency. In other embodiments, a metallic insert may be coupled to the distal end 100D after formation of bone screw 100 by a 2D or 3D printing process.

Figure 2:
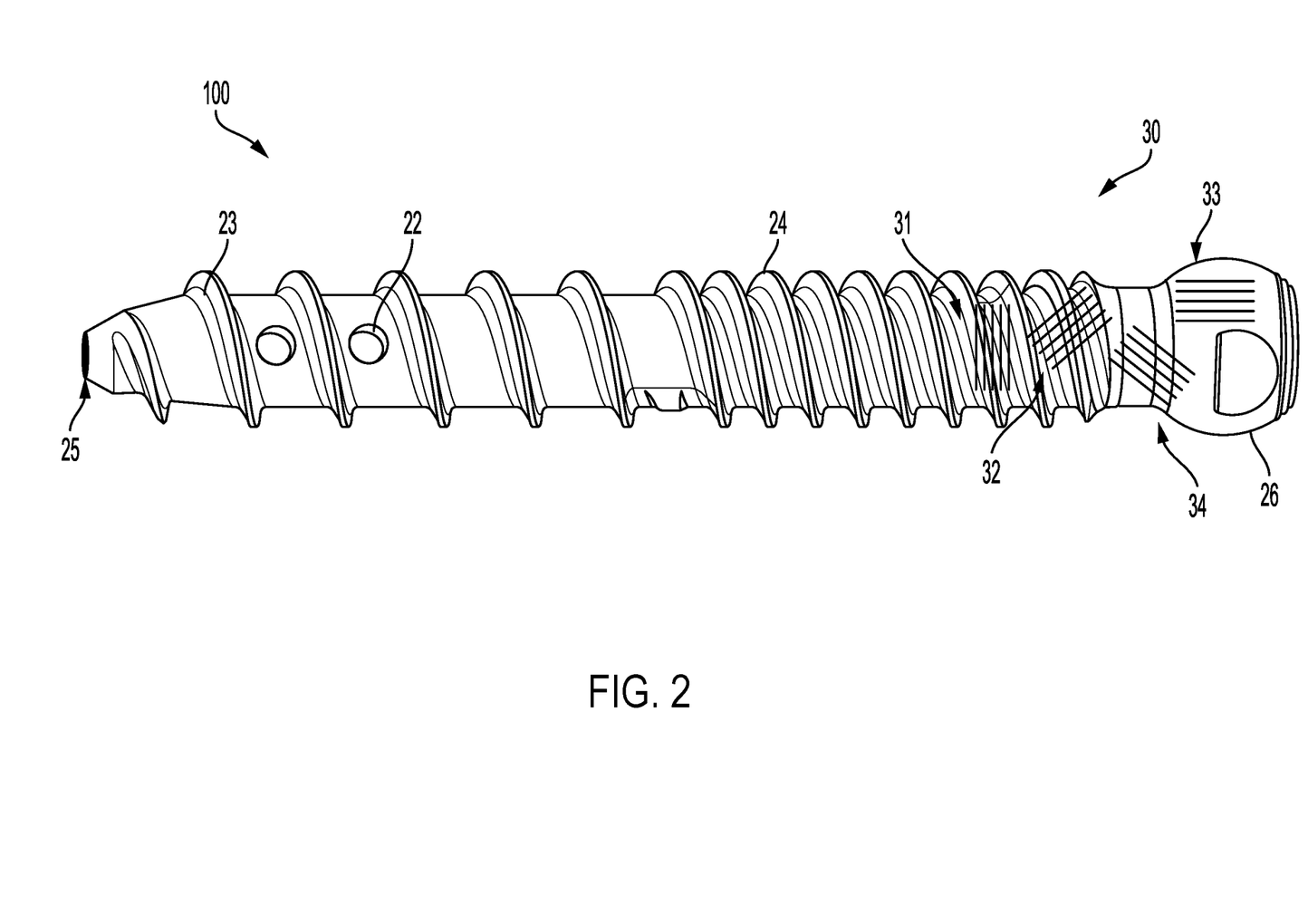
FIG. 2 is a side view of a bone screw showing example orientations of continuous fibers.

FIG. 2 is a side view of a bone screw 100 showing various example orientations of continuous fibers 30 in relation to longitudinal axis L-A of bone screw 100 (see FIG. 1). For example, fibers 33 may be oriented parallel with the longitudinal axis L-A at a 0-degree relative orientation; fibers 32 may be oriented at a +45 degree relative orientation with respect to the longitudinal axis L-A; fibers 34 may be oriented at a −45 degree relative orientation with respect to the longitudinal axis L-A; and fibers 31 may be oriented at a 90 degree orientation with respect to the longitudinal axis L-A. It shall be appreciated that select portions of bone screw 100 may be formed by orienting fibers in any of the various orientations disclosed herein, e.g., one portion may be formed by fibers oriented by a first degree and a different portion may be formed by fibers oriented at a second degree different than the first degree. Computer simulations, such as Finite Element Analysis, may be performed on the desired portion or part to determine stress directions in the portion or part, and these simulations may then serve as the basis for determining the direction and/or orientation of the fibers. For example, if the analysis determines that stress or strain is concentrated in the X direction then the fibers may be generally oriented in the X direction). In a different example, where analysis determines that the stress or strain direction changes along the length and/or geometry of the component, than the fibers may also be oriented differently to maximize strength in the direction of the expected stress or strain at that particular location, e.g., continuously changing the fiber orientation to maximize strength in discrete regions of a component on an as needed basis.

Figure 3A:
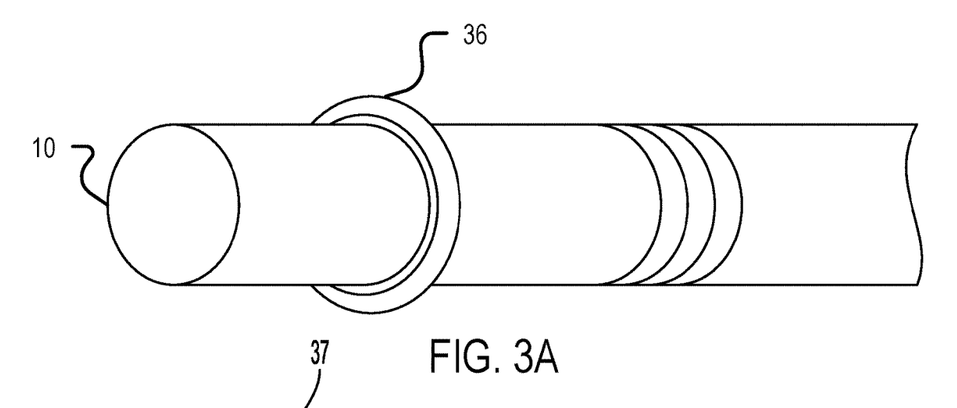
FIG. 3A is a side view of a circumferential fiber orientation.
Figure 3B:
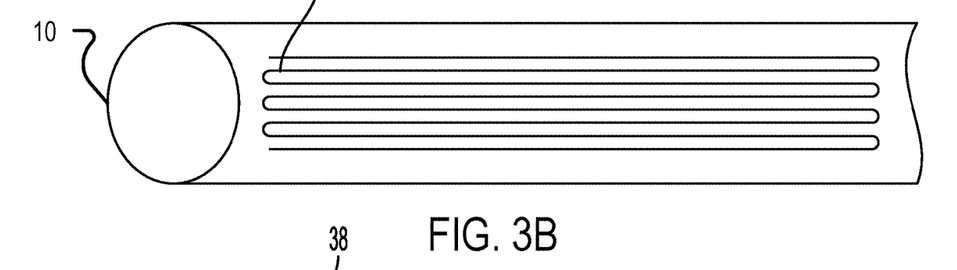
FIG. 3B is a side view of a longitudinal fiber orientation.
Figure 3C:
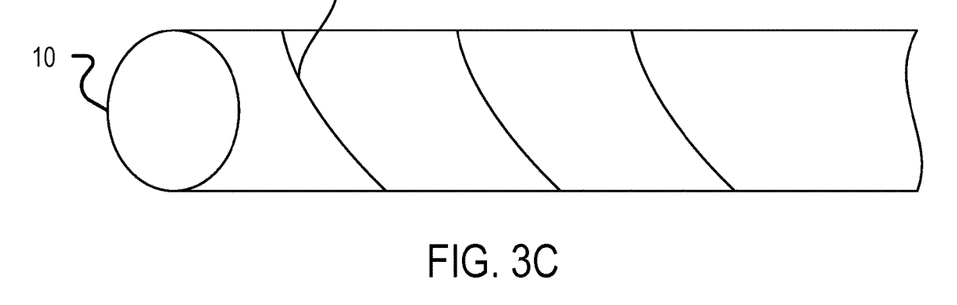
FIG. 3C is a side view of a helical fiber orientation.

FIGS. 3A-3C show various layering techniques and orientations of continuous fibers. FIG. 3A is a side view showing substrate 10 and a circumferential continuous fiber orientation 36. FIG. 3B is a side view showing substrate 10 and a longitudinal continuous fiber orientation 37. FIG. 3C is a side view showing substrate 10 and a helical continuous fiber orientation 38.

Figure 4:
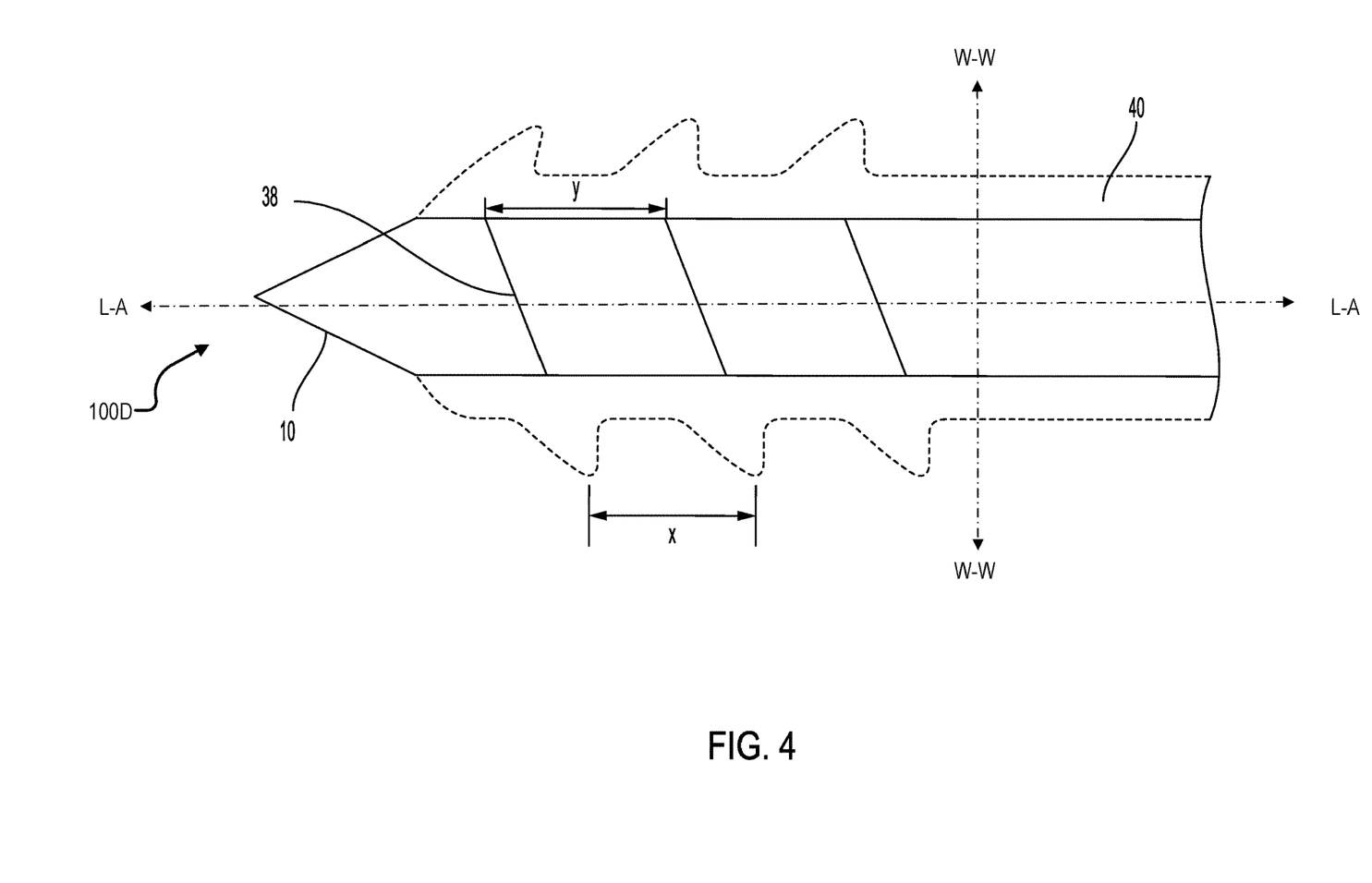
FIG. 4 is a side view of a helical fiber formation process.

FIG. 4 is a side view of an example formation process for a helical continuous fiber orientation 38. In the example embodiment, a continuous fiber may be layered on top of substrate 10 in a helical pattern around substrate 10. In some embodiments, substrate 10 may be supported at the proximal end 100P and distal end 100D and in other embodiments, substrate 10 may be stood vertically up, for example see FIG. 8. In various embodiments, a continuous fiber may be layered in a helical pattern by moving an orifice of a nozzle or extruder in a corresponding helical pattern around the substrate 10. For example, movement of an extruder orifice or tip may be controlled by a 3D printing machine or process. In various embodiments, an extruder may extrude the continuous fibers as single strands and in other embodiments the continuous fibers may be surrounded and/or impregnated in a thermoplastic and extruded onto substrate 10. For example, a continuous fiber matrix may comprise continuous fibers and a carrier, e.g., molten thermoplastic, that may be extruded onto substrate 10 and harden when cooled.

In some embodiments, substrate 10 may be referred to as a first portion and the layering of helical continuous fibers 38 may form a second portion 40 (shown in dashed lines) that is coupled to and/or adhered to substrate 10. In various embodiments, the layering of helical continuous fibers 38 may form a second portion 40 (shown in dashed lines) that is printed on top of substrate 10 in a second operation by a 3D printing process. In other embodiments, the substrate 10 and second portion 40 may be printed together using two print heads or two nozzles operating in a coordinating and simultaneous manner. In other embodiments still, the second portion 40 may be printed separately from substrate 10 and be adhered to substrate 10 after printing is completed. In this embodiment, the second portion 40 may include a central void space or cavity having a size and shape generally corresponding to a size and shape of the substrate 10.

In the example embodiment, a distance between helical continuous fibers 38 in the longitudinal direction (may also be referred to as pitch) may be represented as Y and the helical fibers 38 may be sequentially stacked on top of one another until the second portion 40 is formed. For example, a first layer may consist of laying a first continuous helical fiber 38 from the proximal end 100P to the distal end 100d. Thereafter, a second layer may consist of laying a second continuous helical fiber 38 from the proximal end 100P to the distal end 100D. Over time, a plurality of sequentially stacked layers comprising continuous helical fibers 38 may be built up on top of one another until the second portion 40 is formed. In various embodiments, the entirety of second portion 40 is formed by layering continuous helical fibers 38 from the proximal end 100P to the distal end 100D, e.g., in the same direction. In an alternate embodiment, a first layer may be formed by layering continuous helical fibers 38 from the proximal end 100P to the distal end 100D, and then layering a second layer of continuous helical fibers 38 from the distal end 100D to the proximal end 100P, e.g., each layer of the plurality of layers is formed in an opposite layer from the immediately prior layer. In the example method of manufacture, a distance between continuous helical fibers 38 for a first layer, represented as Y, may of course be varied in a subsequent layer. Similarly, a position where the continuous helical fibers 38 begin and end may be varied such that the final shape of second portion 40 may take the shape of a thread pattern having a final pitch, represented as X, and any thread angle and depth of thread appropriate.

Figure 5A:
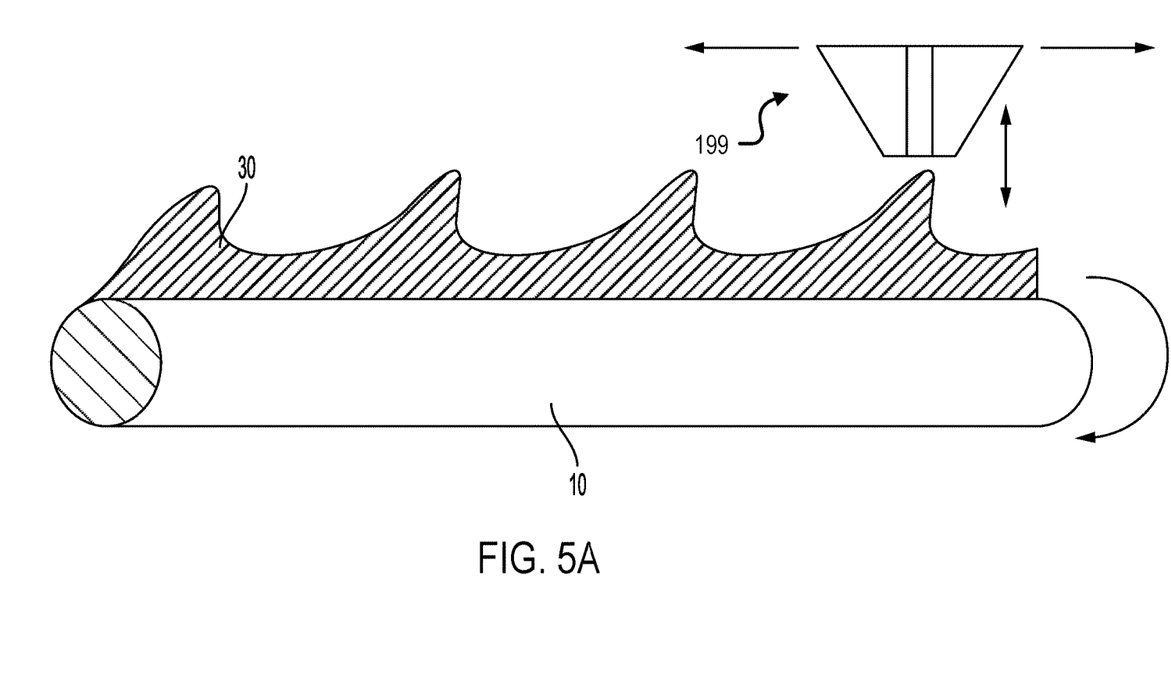
FIG. 5A is a side view of a substrate and a 3D printing schematic.

FIG. 5A is a side view schematic of a substrate 10 and a nozzle 199 for an extruder and/or 3D printer. In the example embodiment, continuous fibers 30 may be layered on top of substrate 10 in any of the various geometrical orientations as explained above. However, in the example embodiment, substrate 10 may be connected to a mandrel or a lathe and the substrate 10 may therefore rotate (represented by arrow). In the example embodiment, the nozzle 199 may move forward and backward, side to side, and up and down, e.g., in the typical cartesian coordinate system X, Y, Z. In this method of manufacture, the substrate 10 may be rotating at a particular rotations per minute (RPM) and the nozzle 199 may be positioned above substrate 10. While the substrate 10 is rotating at a pre-determined RPM, the nozzle 199 may begin extruding continuous fibers and/or a continuous fiber matrix in the longitudinal direction from the proximal end 100P towards the distal end 100D. The rate that nozzle 199 moves in the longitudinal direction may be timed according to the pre-determined RPM such that the fibers are layered in a helical pattern, a diagonal pattern, alternating diagonal pattern, etc. It shall be understood, that in some embodiments various parts and components may remain stationary and the nozzle 199 may move with 6 degrees of freedom around the part. For example, a robotic armature having at least six degrees of freedom may manipulate the nozzle 199 orifice as needed.

Figure 5B:
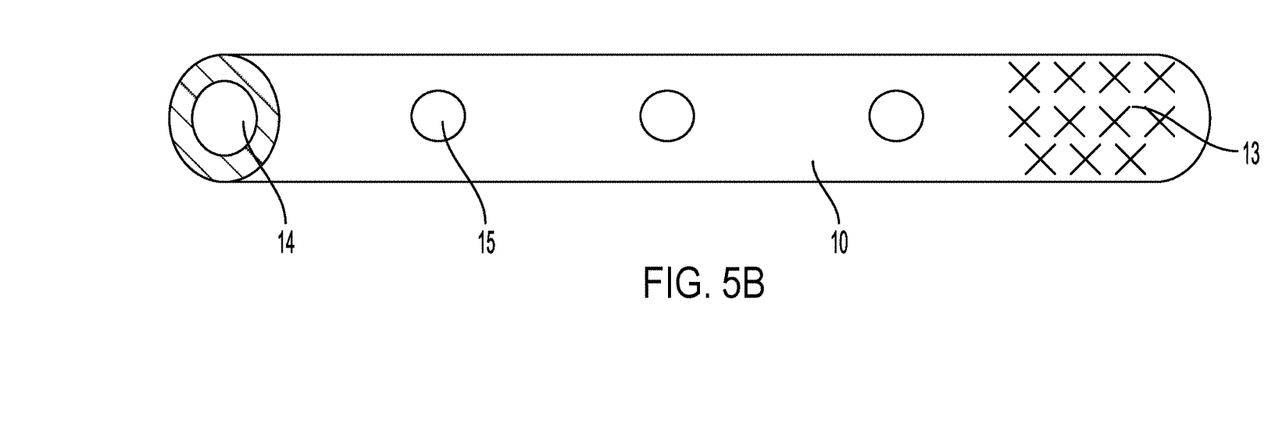
FIG. 5B is a side view of an alternate substrate having surface texture.

FIG. 5B is a side view of an alternate substrate 10. In the example embodiment, substrate 10 may include apertures 15 that extend through a sidewall of substrate 10. In some embodiments, apertures 15 may facilitate the coupling and/or adhesion of continuous fibers from nozzle 199, for example. In other embodiments, apertures 15 may be utilized as fenestrations and continuous fibers from nozzle 199 may be layered around apertures 15 such that they remain open. In other embodiments still, apertures 15 may be filled with an alternate material, e.g., a metallic material, to serve as a fiducial marker that may be disposed within aperture 15 and subsequently covered by continuous fibers 30 during the formation of bone screw 100. Substrate 10 may include an aperture 14 at a proximal end 100P or distal end 100D. Aperture 14 may extend in the longitudinal direction for any relative distance, e.g., the entire distance from proximal end 100P to distal end 100d or a select portion thereof. In at least one embodiment aperture 14 may only extend a relatively short distance and terminate anywhere between 5%-50% of the length of substrate 10. In this embodiment, aperture 14 may be used to socket, adhere, or otherwise couple an additional element, for example a metallic tip or a fiducial marker. In other embodiments, aperture 14 may extend for a relatively greater distance anywhere between 100% and 50% of the length of substrate 10. In this embodiment, aperture 14 may serve as a conduit tying into apertures 15 to facilitate boney ingrowth and/or a pathway for bone growth promoting material. In some embodiments, apertures 14, 15 may be filled with Fenestrated Screw Cement, such as that sold by Medtronic under the brand name HV-R™ or a Bone Cement such as that sold by Medtronic under the brand name Kyphon™ Xpede™, for example. In various embodiments, apertures 14, 15, may be formed during a mold in place or casting mold process or they may be formed afterwards by a machining process and/or a drilling process, for example.

Additionally, in some embodiments substrate 10 may have surface texturing 13 to facilitate adhesion between substrate 10 and the continuous fibers 30. In the example embodiment, surface texturing 13 is of a cross type or X type hatching. In other embodiments, surface texturing 13 may be a diamond tread or longitudinally extending striations, for example. In various embodiments, surface texturing 13 may be formed by an etching process and/or grit blasting process to create a high friction surface.

Figure 6:
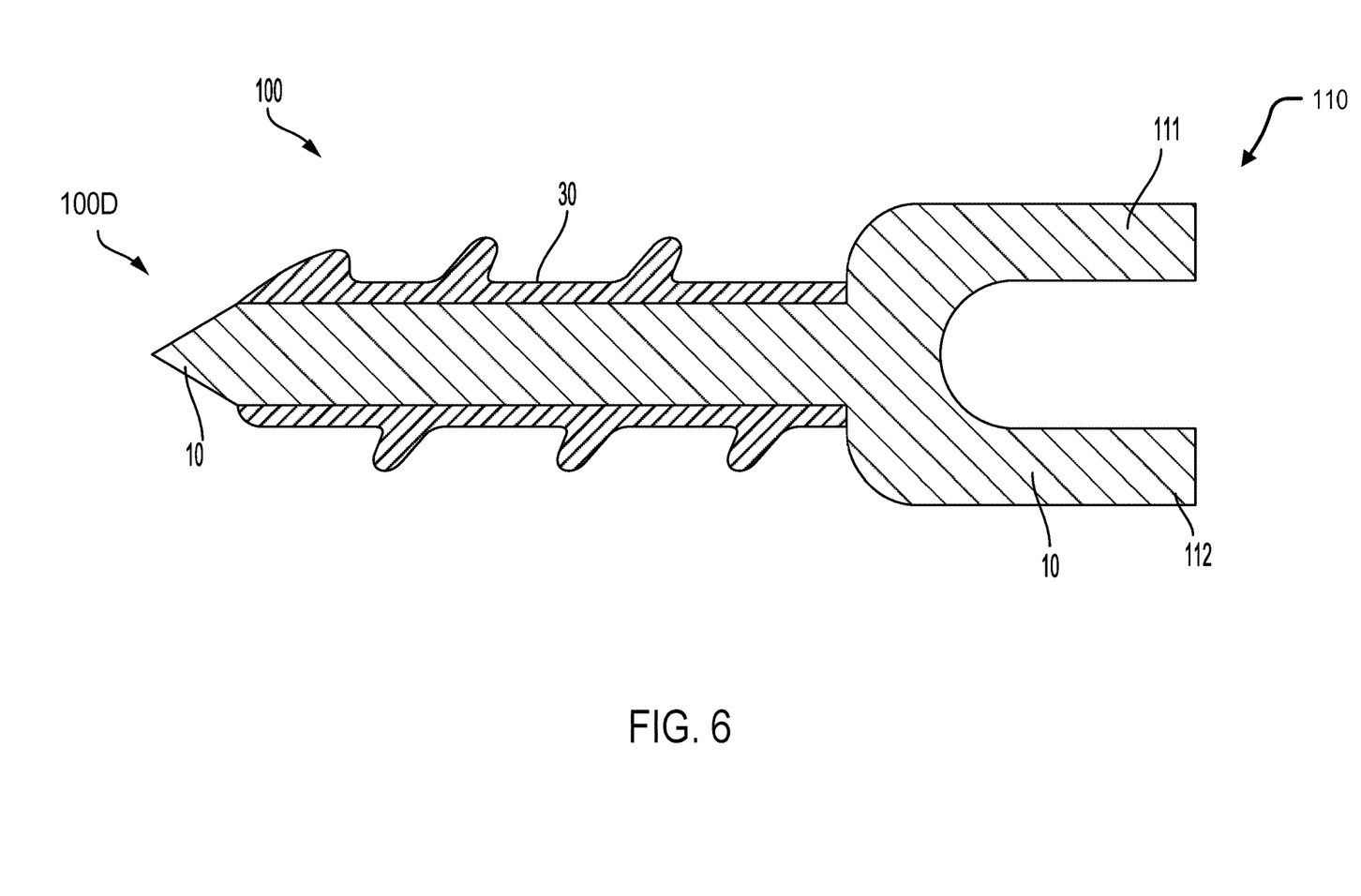
FIG. 6 is a side view of a bone screw having a receiver head portion.

FIG. 6 is a side view of a bone screw 100 having a receiver head portion 110. In various embodiments, different types of head portions 110 may be formed than those specifically shown. In at least one embodiment, receiver head portion 110 may be used to capture a rod extending through a first arm 111 and second arm 112. In the example embodiment, bone screw 100 includes a substrate 10, as explained previously, and substrate 10 includes the receiver head portion 110. In some instances, it may be difficult to 3D print receiver head portion 110 and accordingly there are advantages to having receiver head portion 110 be an integral part of substrate 10. For example substrate 10 including the receiver head portion 110 may be formed by a thermoplastic molding process, e.g., by the various molding processes disclosed in U.S. Pat. No. 7,850,717, the entire contents of which are incorporated herein by reference, e.g., injection molding, overmolding, plastic injection molding, and/or metal injection molding.

In some embodiments, the distal most tip 100D of bone screw 100 may be covered and/or surrounded by continuous fibers 30. For example, the distal most tip 100D, corresponding to a leading tip of bone screw 100 distal of the threads, may be formed of continuous fibers 30 that extend in a longitudinal direction. As illustrated in FIG. 2 of U.S. Pat. No. 7,850,717, the entire contents of which are incorporated herein by reference, bone interface portion 18 may be formed of a rigid material such as continuous fibers 30 and surround core portion 16, which may be formed of a PEEK material, e.g. At least one advantage of having the leading tip of bone screw 100 be formed of and/or surrounded by continuous fibers 30 may be an increase in the rigidity of the leading tip while also allowing for a plastic interface with boney anatomy.

Figure 7:
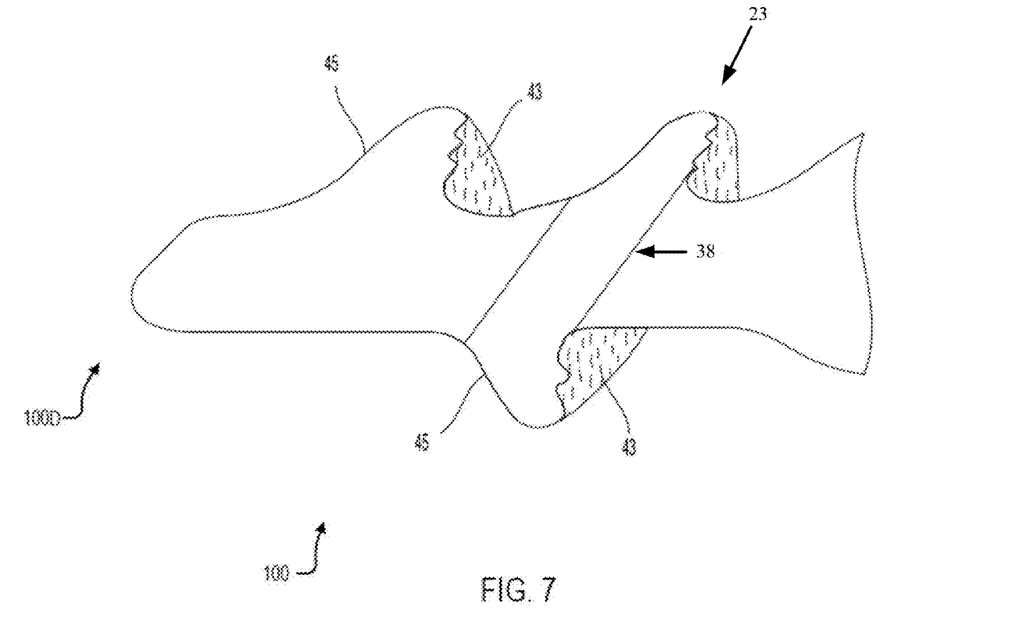
FIG. 7 is a side view of a distal region of a bone screw having surface texturing.

FIG. 7 is a side view of a distal region 100D of a bone screw 100 having surface texturing. In the example embodiment, a helical thread pattern of bone screw 100 may include an upper surface 43 facing the proximal end 100D and a lower surface 45 opposite the upper surface 43 and facing the distal end, 100D. In various embodiments, upper surface 43 may include surface texturing features. For example, a high friction surface comprising dimpling, striations, channeling and ridges, and/or a diamond tread pattern, for example. In some embodiments, upper surface 43 may be formed during a 3D printing process, e.g., by nozzle 199 scraping the uppermost exposed layer or by nozzle 199 printing a friction surface. In some embodiments, upper surface 43 may undergo a grit blasting or chemical etching process after bone screw 100 is formed. At least one advantage of having the upper surface 43 include a high friction surface is that it may cause bone screw 100 to bite down and/or facilitate drawing or pulling bone screw 100 forward when rotated.

Figure 8:
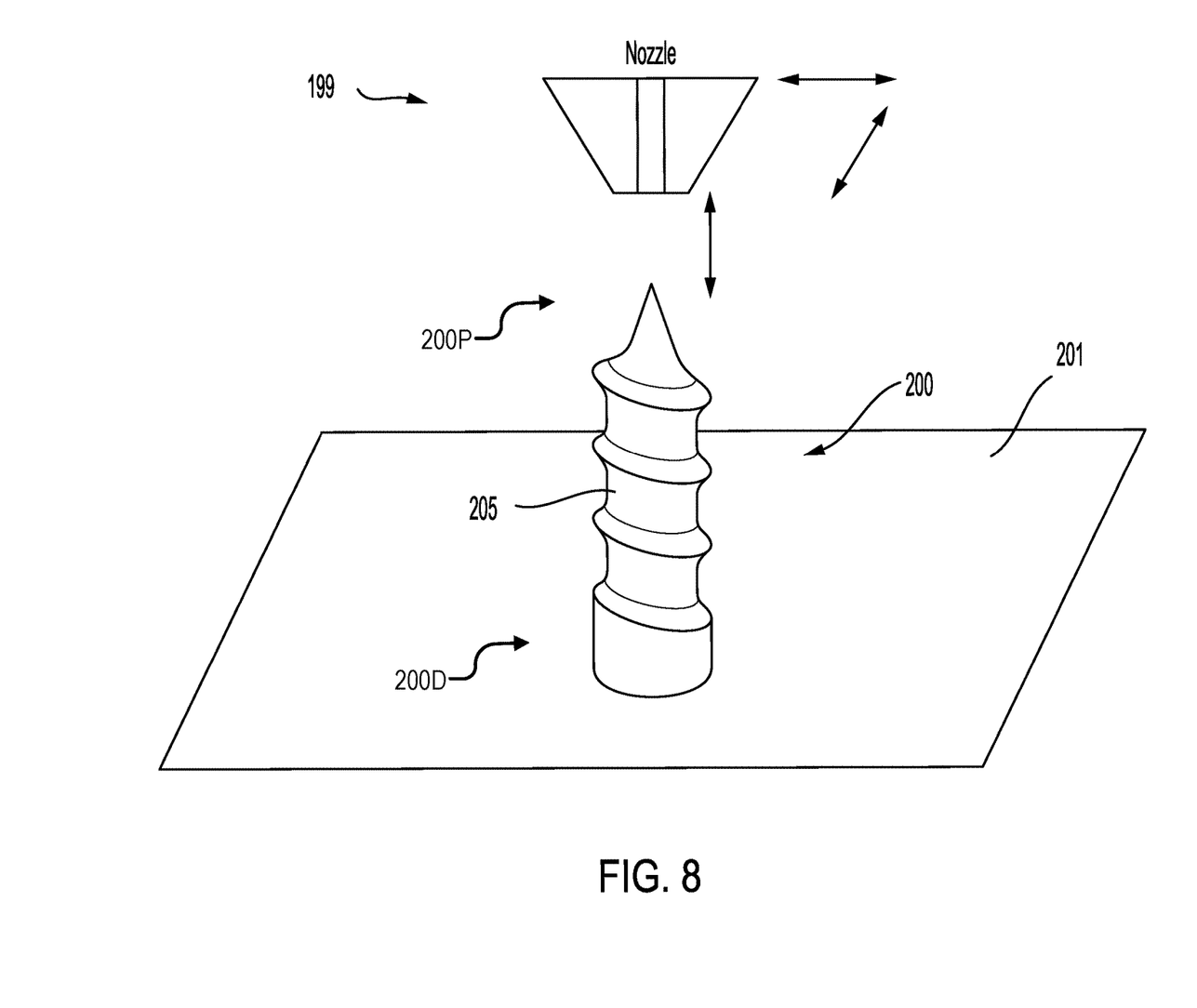
FIG. 8 is a schematic of a 3D printing process.
Figure 9A:
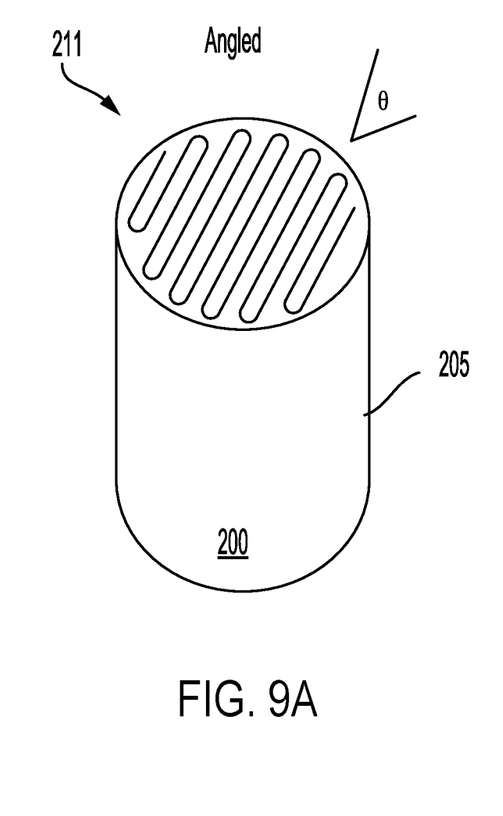
FIG. 9A illustrates an angled continuous fiber orientation.
Figure 9B:
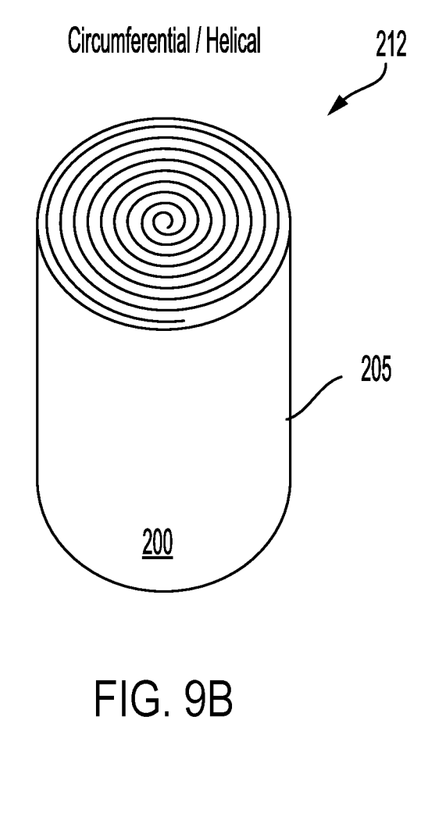
FIG. 9B illustrates a circumferential/helical continuous fiber orientation.
Figure 9C:
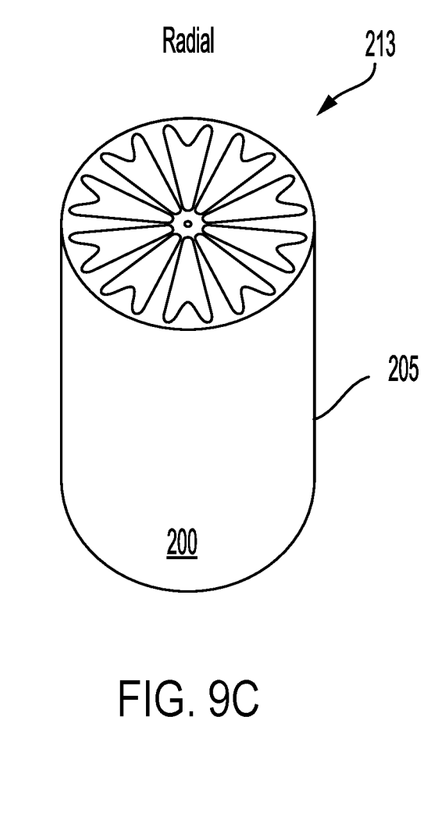
FIG. 9C illustrates a radial continuous fiber orientation.

FIG. 8 is a schematic of a 3D printing process. In the example process, bone screw 200 is a monolithic component formed entirely by a 3D printing process. Bone screw 200 may include many of the same, similar, and/or substantially similar features as bone screw 100. Bone screw 200 may be formed by a nozzle 199 of a 3D printer and/or extruder depositing continuous fibers as explained previously. However, the method of deposition may consist of forming a plurality of sequentially stacked layers one on top of the next in a vertical direction, for example. In at least one method of manufacture, a plurality of sequentially stacked layers of continuous fibers may be layered from a distal end 200D to a proximal end 200P in a longitudinal direction (vertical direction) and extend between sidewall surfaces 200S in a lateral direction (horizontal direction). A first layer may be formed on a plate 201 and each subsequent layer may be deposited on top of the immediately prior layer, for example. In various embodiments, each layer may refer to at least one continuous fiber or continuous fiber matrix extending from side to side of bone screw 200 in a lateral direction, e.g., each layer may extend for a height in the vertical direction and define the sidewall surfaces 200s of bone screw 200 at the corresponding elevation. In the example embodiment of FIG. 9, each layer may be formed by an angled continuous fiber orientation 211 that is angled with respect to a plane bisecting bone screw 200 from proximal end 200P to distal end 200D along longitudinal axis L-A. For example, a first layer defining the distal end 100D may be formed by an angled continuous fiber orientation 211, and thereafter each subsequent layer may be formed on top of the immediately prior layer. FIG. 9B illustrates a circumferential/helical continuous fiber orientation 212. In this embodiment, nozzle 199 may begin laying a first layer from a center point corresponding to the longitudinal axis in a concentric helical pattern moving radially outward towards the sidewall surfaces 200s. Thereafter, each subsequent layer may be formed on top of the immediately prior layer. FIG. 9C illustrates a radial continuous fiber orientation 213. In the example embodiment, a first layer may be formed by laying a continuous fiber from a center point corresponding to the longitudinal axis to a sidewall surface 200s, back to the center point and then back to the sidewall surface 200s repeating the path of travel until the first layer is fully formed. Thereafter, each subsequent layer may be formed on top of the immediately prior layer. It shall be understood that various bone screws 100, 200 may be printed by any combination of the aforementioned continuous fiber patterns. For example, a first layer may comprise continuous fibers oriented in any of the example orientations, a second layer may comprise fibers oriented in any of the example orientations, a third layer may comprise fibers oriented in any of the example orientations, etc.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. A bone screw, comprising:
an elongate part having a longitudinal axis extending in a longitudinal direction from a first end to a second end of the bone screw, and comprising:
a base substrate extending between the first end and the second end, and along the longitudinal axis; and
a plurality of continuous fiber layers disposed on the base substrate such that each of the continuous fiber layers at least partially surrounds the base substrate;
wherein first layers of the plurality of continuous fiber layers comprise helical continuous fibers and define at least part of a first portion of an exposed thread pattern of a shaft of the bone screw;
wherein second layers of the plurality continuous fiber layers define a second portion of the exposed thread pattern that is longitudinally offset or spaced apart from the first portion of the exposed thread pattern, the second layers comprising fibers oriented in a direction relative to the longitudinal axis that is different than an orientation of the helical continuous fibers of the first layers;
wherein a distance between the helical continuous fibers in a first one of the first layers is different than a distance between the helical continuous fibers in a second one of the first layers; and
wherein the plurality of continuous fiber layers comprises an alternating sequence of a first layer type and a second layer type, at least one of the first or second layers being of the first layer type including continuous fibers that are diagonally oriented at about +45 degrees with respect to the longitudinal axis, and at least one of the first layers or a third layer being of the second layer type including continuous fibers that are diagonally oriented at about -45 degrees with respect to the longitudinal axis.

2. The bone screw of claim 1, wherein the plurality of continuous fiber layers comprises at least one third layer of continuous fibers that are circumferentially oriented with respect to the base substrate.

3. The bone screw of claim 1, wherein the plurality of continuous fiber layers comprises at least one third layer of continuous fibers that are helically oriented with respect to the base substrate.

4. The bone screw of claim 1, wherein the plurality of continuous fiber layers comprises at least one third layer of continuous fibers that are longitudinally oriented with respect to the base substrate.

5. The bone screw of claim 1, wherein other fibers of the first layers of the plurality of continuous fiber layers are diagonally oriented at about +45 degrees with respect to the longitudinal axis, and the fibers of the second layers of the plurality of continuous fibers are diagonally oriented at about -45 degrees with respect to the longitudinal axis.

6. The bone screw of claim 1, wherein the base substrate comprises an aperture at the distal end.

7. The bone screw of claim 1, wherein a fiducial marker is disposed in an aperture of the bone screw.

8. The bone screw of claim 1, wherein:
the base substrate comprises at least one aperture in a sidewall thereof that is exposed.

9. The bone screw of claim 1, wherein:
the base substrate comprises a first aperture extending through a center thereof in the longitudinal direction, the base substrate further comprising at least one second aperture in a sidewall thereof adjoining the first aperture, and
the plurality of continuous fiber layers leave the first aperture and the at least one second aperture exposed.

10. The bone screw of claim 1, wherein: the second portion further defines a head comprises a drive cavity for driving the bone screw.

11. The bone screw of claim 1, wherein the base substrate comprises an end including a first arm and a second arm.

12. The bone screw of claim 1, wherein the plurality of continuous fiber layers comprises a 3D printed material with extruded continuous fibers positioned around the base substrate.

13. The bone screw of claim 1, wherein the plurality of continuous fiber layers comprises a 3D printed material comprising a continuous fiber matrix including a thermoplastic material surrounding the continuous fibers.

14. The bone screw of claim 1, wherein the plurality of continuous fiber layers comprises a 3D printed material comprising a continuous fiber matrix of alternately oriented fibers.

15. The bone screw of claim 1, wherein the second end of the bone screw is formed of or surrounded by third layers of the plurality of continuous fiber layers to provide a leading tip with rigidity while allowing a malleable material to interface with boney anatomy.

16. The bone screw of claim 15, wherein the malleable material comprises plastic.

* * * * *